(12) United States Patent
Kawata et al.

(10) Patent No.: US 10,988,403 B2
(45) Date of Patent: Apr. 27, 2021

(54) LOW MELTING POINT GLASS COMPOSITION EXCELLENT IN WATER RESISTANCE

(71) Applicant: SHOFU INC., Kyoto (JP)

(72) Inventors: Keita Kawata, Kyoto (JP); Masanori Goto, Kyoto (JP); Kenji Kono, Kyoto (JP)

(73) Assignee: SHOFU INC., Kyoto (JP)

( * ) Notice: Subject to any disclaimer, the term of this patent is extended or adjusted under 35 U.S.C. 154(b) by 0 days.

(21) Appl. No.: 16/256,072

(22) Filed: Jan. 24, 2019

(65) Prior Publication Data
US 2019/0322567 A1  Oct. 24, 2019

(30) Foreign Application Priority Data

Jan. 26, 2018 (JP) ................................ JP2018-11983

(51) Int. Cl.
C03C 3/087 (2006.01)
A61C 8/00 (2006.01)
C03C 3/093 (2006.01)

(52) U.S. Cl.
CPC ............ *C03C 3/087* (2013.01); *A61C 8/0015* (2013.01); *C03C 3/093* (2013.01); C03C 2201/10 (2013.01); C03C 2201/12 (2013.01); C03C 2201/32 (2013.01); C03C 2201/42 (2013.01)

(58) Field of Classification Search
CPC ..... C03C 3/093; C03C 3/118; C03C 2201/32; C03C 2201/10; C03C 4/0021; C03C 14/00; C03C 4/20; A61C 8/0015; A61K 6/833; A61K 6/836
See application file for complete search history.

(56) References Cited

U.S. PATENT DOCUMENTS

| 5,176,747 | A  | * | 1/1993 | Panzera | A61K 6/822 |
|           |    |   |        |         | 106/35 |
| 5,204,291 | A  |   | 4/1993 | Nigrin  | |
| 5,314,334 | A  | * | 5/1994 | Panzera | A61K 6/807 |
|           |    |   |        |         | 433/206 |
| 6,554,615 | B1 |   | 4/2003 | Brodkin et al. | |
| 2012/0219792 | A1 |   | 8/2012 | Yamamoto et al. | |
| 2014/0106168 | A1 | * | 4/2014 | Ritter  | A61K 6/824 |
|           |    |   |        |         | 428/392 |
| 2017/0281473 | A1 | * | 10/2017 | Takeuchi | A61K 6/802 |

FOREIGN PATENT DOCUMENTS

| CA | 2 351 154 | 12/2001 |
| GB | 1054297 | 1/1967 |
| JP | 2002-53339 | 2/2002 |
| JP | 4209946 | 10/2008 |
| JP | 2009-185001 | 8/2009 |
| JP | 4481937 | 3/2010 |
| JP | 4716633 | 4/2011 |
| WO | 97/30678 | 8/1997 |
| WO | 01/01924 | 1/2001 |

OTHER PUBLICATIONS

Extended European Search Report dated Aug. 12, 2019 in corresponding European Patent Application No. 19153540.0.

\* cited by examiner

*Primary Examiner* — Noah S Wiese
(74) *Attorney, Agent, or Firm* — Wenderoth, Lind & Ponack, L.L.P.

(57) ABSTRACT

To provide a glass composition which can be used for a dental porcelain or a dental ceramics coloring material, and has low temperature meltability, acid resistance and preservation stability under the humid environment which are required for a dental porcelain or a dental ceramics coloring material, and a dental porcelain and dental ceramics coloring material which contain the glass composition of the present disclosure. To provide a low melting glass composition with softening point (Ts) less than 600° C. comprising as a component; $SiO_2$: 55.0 to 75.0 wt. %, $B_2O_3$: 6.1 to 12.0 wt. %, $Al_2O_3$: 2.0 to 8.0 wt. %, ZnO: 2.0 to 8.5 wt. % and two or more kinds of alkali metal oxide: 10.5 to 20.0 wt. %.

10 Claims, No Drawings

LOW MELTING POINT GLASS COMPOSITION EXCELLENT IN WATER RESISTANCE

CROSS-REFERENCE TO RELATED APPLICATIONS

This application is based on and claims the benefit of priority from Japanese Patent Application Serial No. 2018-11983 (filed on Jan. 26, 2018), the contents of which are hereby incorporated by reference in their entirety.

BACKGROUND OF THE INVENTION

Field of the Invention

The present disclosure relates to a low melting glass composition which can be used for a dental porcelain material or a dental ceramics coloring material.

Description of the Related Art

A dental porcelain material is a glass ceramics material comprising feldspar and the like as a raw material and is mainly used for a crown prosthesis restoration of a missing tooth. The dental porcelain material is classified into a metal bonding porcelain material which is baked on a metal frame for use and a zirconia porcelain material baked on a zirconia frame for use, by method of use, and a prosthesis device may be prepared from only a dental porcelain material.

A dental ceramics coloring material comprises a glass material or a glass ceramics material as a base material same as the dental porcelain material and is compounded with a various coloring material ingredient (pigment). The dental ceramics coloring material is used for a color tone adjustment of a dental porcelain material and a dental ceramics material (alumina and zirconia, etc.).

Low temperature meltability which enables an application to various core materials (metal, lithium silicate glass ceramics, zirconia and mica glass ceramics, etc.) and acid resistance which is required for long-term stability in the oral cavity, etc. are exemplified as the character required for a dental porcelain material and a dental ceramics coloring material in recent year. In addition, preservation stability under the humid environment has been required for restraining performance deterioration by aged deterioration of a dental porcelain material and a dental ceramics coloring material.

Japanese Patent No. 4716633 discloses a dental porcelain material composition consisting of an amorphous glass phase having a calcination temperature less than 850° C.

Japanese Patent No. 4716633 includes the description that boron oxide ($B_2O_3$) has an action to lower a thermal expansion coefficient and a calcination temperature.

Because all compositions described in Japanese Patent No. 4716633 include boron oxide ($B_2O_3$) within a range of 2.6 to 6.0 wt. %, it is difficult to satisfy a softening point (Ts) less than 600° C. in any composition of the Japanese Patent No. 4716633.

Japanese Unexamined Patent Application Publication No. 2002-53339 discloses a low temperature sintering potassium-zinc-silicate glass.

In the composition described in Japanese Unexamined Patent Application Publication No. 2002-53339, low temperature meltability is imparted to a glass skelton consisting of silicon oxide ($SiO_2$) by two kinds of alkali metal. However, because the composition includes a large quantity (8.5 to 20.0 wt. %) of zinc oxide (ZnO), it is difficult in the composition to maintain acid resistance and preservation stability under the humid environment.

Japanese Patent No. 4209946 discloses a low melt temperature porcelain material composition which is used for an artificial tooth and has 11.5 to $12.5 \times 10^{-6} K^{-1}$ [30° C. to 430° C.] of a thermal expansion coefficient.

Because the composition described in Japanese Patent No. 4209946 is imparted with low temperature meltability without containing zinc oxide (ZnO) in the component composition, it is difficult in the composition to maintain acid resistance and preservation stability under the humid environment.

Japanese Unexamined Patent Application Publication No. 2009-185001 discloses a dental porcelain material composition comprising two kinds of vitreous particle containing silicon oxide, aluminum oxide, boron oxide, zinc oxide and sodium oxide as a main component. In the dental porcelain material composition of Japanese Unexamined Patent Application Publication No. 2009-185001, the second vitreous particle has softening point higher than the softening point of the first vitreous particle by 20 to 80° C.

Because the first vitreous particle described in Japanese Unexamined Patent Application Publication No. 2009-185001 contains boron oxide ($B_2O_3$) within a range of 15 to 25 mass %, it is difficult to maintain acid resistance and preservation stability under the humid environment. Further, because the softening point of the second vitreous particle is higher than the softening point of the first vitreous particle by 20° C. or more, it is difficult to satisfy a softening point (Ts) less than 600° C.

Japanese Patent No. 4481937 discloses a dental porcelain material which can be calcined at a temperature within a range of 750 to 900° C. and has a thermal expansion coefficient within a range of 8.8 to $9.0 \times 10^{-6}$/° C. in the temperature within a range of 30 to 450° C. after calcination.

The composition described in Japanese Patent No. 4481937 contains $Sb_2O_3$ and $CeO_2$ as an essential element in order to restrain the yellowing of the dental porcelain material.

In any prior arts, it is impossible to achieve a softening point (Ts) less than 600° C. while maintaining high acid resistance and excellent preservation stability under the humid environment.

SUMMARY OF THE INVENTION

Technical Problem

The present disclosure provides a glass composition which can be used for a dental porcelain material or a dental ceramics coloring material, and has low temperature meltability, acid resistance and preservation stability under the humid environment which are required for a dental porcelain material or a dental ceramics coloring material, and a dental porcelain material and a dental ceramics coloring material which contain the glass composition of the present disclosure.

Solution to Problem

The low melting glass composition of the present disclosure is a low melting glass composition with a softening point (Ts) less than 600° C. comprising as a component;
$SiO_2$: 55.0 to 75.0 wt. %,
$B_2O_3$: 6.1 to 12.0 wt. %, Al$_2$O$_3$: 2.0 to 8.0 wt. %,
ZnO: 2.0 to 8.5 wt. % and
two or more kinds of alkali metal oxide: 10.5 to 20.0 wt. %.

It is preferable that the low melting glass composition of the present disclosure further comprises at least one of following component;
MgO: 3.0 wt. % or less,
CaO: 3.0 wt. % or less,
ZrO$_2$: 4.0 wt. % or less,
TiO$_2$: 3.0 wt. % or less, and
F: 2.0 wt. % or less.

It is preferable in the low melting glass composition of the present disclosure that a thermal expansion coefficient in the temperature within a range of 25° C. to 400° C. based on ISO 6872:2015 is within a range of 7.0 to 11.0×10$^{-6}$ K$^{-1}$.

It is preferable in the low melting glass composition of the present disclosure that a dissolution amount to an acid based on ISO 6872:2015 is 35 µg/cm$^2$ or less.

The present disclosure further provides a dental porcelain compounded with the low melting glass composition of the present disclosure.

The present disclosure further provides a dental ceramics coloring material compounded with the low melting glass composition of the present disclosure.

Advantageous Effects of Invention

In a dental porcelain material and a dental ceramic coloring material which use the low melting glass composition of the present disclosure as a base material, it is possible to set a calcination temperature lower than the calcination temperature of various core materials which becomes a substrate (metal, lithium silicate glass ceramics, zirconia, leucite glass ceramics and mica glass ceramics, etc.). Therefore, it is possible to use at a low temperature which does not cause a deformation of the substrate.

A dental porcelain material which use the low melting glass composition of the present disclosure as a base material can be suitably used for a core material which has a low calcination temperature and has a thermal expansion coefficient within a range of 8.0 to 13.0×10$^{-6}$ K$^{-1}$ such as lithium silicate glass ceramics and zirconia which has the matching thermal expansion coefficient.

Because a dental ceramics coloring material which use the low melting glass composition of the present disclosure as a base material has a low calcination temperature, it is insusceptible to an influence of a stress by the difference in the thermal expansion coefficient of the used material. Therefore, it can be used for various core materials and a dental porcelain material used therefor. More preferably, it can be used for lithium silicate glass ceramics, zirconia, a dental porcelain material for lithium silicate glass ceramics and a dental porcelain material for zirconia.

Because a dental porcelain material and a dental ceramics coloring material which use the low melting glass composition of the present disclosure as a base material has excellent acid resistance, it is possible to use stably for a long period of time in an oral cavity.

In a dental porcelain material and a dental ceramics coloring material which use the low melting glass composition of the present disclosure as a base material, there is almost no degradation of the quality by the environmental factor such as humidity.

DETAILED DESCRIPTION OF THE PREFERRED EMBODIMENTS

The low melting glass composition of the present disclosure has a feature that the low melting glass composition has a softening point (Ts) less than 600° C. and comprises as a component;
SiO$_2$: 55.0 to 75.0 wt. %,
B$_2$O$_3$: 6.1 to 12.0 wt. %,
Al$_2$O$_3$: 2.0 to 8.0 wt. %,
ZnO: 2.0 to 8.5 wt. % and
two or more kinds of alkali metal oxide: 10.5 to 20.0 wt. %.

The low melting glass composition of the present disclosure preferably comprises as a component;
SiO$_2$: 60.0 to 70.0 wt. %,
B$_2$O$_3$: 6.5 to 9.0 wt. %,
Al$_2$O$_3$: 4.0 to 7.0 wt. %,
ZnO: 2.5 to 6.5 wt. % and
two or more kinds of alkali metal oxide: 12.5 to 19.0 wt. %.

It is preferable that the low melting glass composition of the present disclosure further comprises at least one of following component;
MgO: 3.0 wt. % or less,
CaO: 3.0 wt. % or less,
ZrO$_2$: 4.0 wt. % or less,
TiO$_2$: 3.0 wt. % or less, and
F: 2.0 wt. % or less.

It is preferable that the low melting glass composition of the present disclosure further comprises at least one of following component;
MgO: 0.1 to 3.0 wt. % or less,
CaO: 0.1 to 3.0 wt. % or less,
ZrO$_2$: 0.1 to 4.0 wt. % or less,
TiO$_2$: 0.1 to 3.0 wt. % or less, and
F: 0.1 to 2.0 wt. % or less.

It is preferable that the low melting glass composition of the present disclosure does not comprise other component other than SiO$_2$, B$_2$O$_3$, Al$_2$O$_3$, ZnO, MgO, CaO, ZrO$_2$, TiO$_2$ and F. That is, the low melting glass composition of the present disclosure consists of essential components consisting of SiO$_2$, B$_2$O$_3$, Al$_2$O$_3$ and ZnO and one or more of optional components selecting from the group consisting of MgO, CaO, ZrO$_2$, TiO$_2$, and F.

The low melting glass composition of the present disclosure comprises SiO$_2$ within a range of 55.0 to 75.0 wt. %, preferably within a range of 60.0 to 70.0 wt. %. The existence of SiO$_2$ in the glass contributes to the formation of a glass skelton. When the content of SiO$_2$ is small, acid resistance and preservation stability under the humid environment decrease remarkably. When the content of SiO$_2$ is large, a deposition of crystal mainly comprising SiO$_2$ and a rise of a softening point are caused.

B$_2$O$_3$ is an essential component of the low melting glass composition of the present disclosure and is generally used for lowering a softening point. However, there is tendency that acid resistance and preservation stability under the humid environment decrease by surplus B$_2$O$_3$. In the present disclosure, the content of B$_2$O$_3$ within a range of 6.1 to 12.0 wt. %, preferably within a range of 6.5 to 9.0 wt. % may contribute to both the formation of a glass skelton and the modification of a glass skelton. Therefore, it is possible to lower a softening point without impairing acid resistance and preservation stability under the humid environment.

When the content of $B_2O_3$ is small, it is impossible to satisfy a softening point (Ts) less than 600° C. which is a feature of the present disclosure.

$Al_2O_3$ is an essential component of the low melting glass composition of the present disclosure and is a component for stabilizing the glass composition. In the present disclosure, the content of $Al_2O_3$ within a range of 2.0 to 8.0 wt. %, preferably within a range of 4.0 to 7.0 wt. % may contribute to improving acid resistance and preservation stability under the humid environment. When the content of $Al_2O_3$ is small, acid resistance and preservation stability under the humid environment, which are the features of the present disclosure, decrease remarkably. When the content of $Al_2O_3$ is large, a change in transparency by the crystal deposition and a rise of softening point are caused.

ZnO is an essential component of the low melting glass composition of the present disclosure and has an effect of lowering a softening point of the glass composition. In the present disclosure, the content of ZnO within a range of 2.0 to 8.5 wt. %, preferably within a range of 2.5 to 6.5 wt. % may contribute to lowering a softening point and to preservation stability under the humid environment. When the content of ZnO is small, it is impossible to satisfy a softening point (Ts) less than 600° C. and high preservation stability which are the features of the present disclosure. When the content of ZnO is large, a change in transparency by the deposition of the crystal comprising Zn as a main component and a decrease of acid resistance and preservation stability under the humid environment are caused.

Alkali metal oxide is an essential component of the low melting glass composition of the present disclosure and is added for lowering a softening point of the glass. Specific examples of alkali metal oxide include Li, Na and K. However, the surplus addition of alkali metal oxide causes a decrease of acid resistance and preservation stability under the humid environment. When only one kind of alkali metal oxide is compounded, by the features described above, a relation of tradeoff occurs between a softening point and acid resistance, and between a softening point and the preservation stability. However, by compounding two or more kinds (preferably three of more kinds) of alkali metal oxide, the mixed alkali effect is exhibited. Therefore, it is possible to lower a softening point without impairing acid resistance and to achieve both the lowering of a softening point and preservation stability. In the present disclosure, because the content of two or more kinds of alkali metal oxide is within a range of 10.5 to 20.0 wt. %, preferably the content of three or more kinds of alkali metal oxide is within a range of 10.5 to 20.0 wt. %, more preferably the content of three or more kinds of alkali metal oxide is within a range of 12.5 to 19.0 wt. %, it is possible to lower a softening point without impairing acid resistance and preservation stability under the humid environment. When a softening point (Ts) less than 600° C. which is a feature of the present disclosure is achieved in the composition which contains a small content of alkali metal oxide, a decrease of acid resistance is caused. On the other hand, when the content of alkali metal oxide is large, a decrease of acid resistance and preservation stability under the humid environment are caused.

It is preferable that the low melting glass composition of the present disclosure contains 3.0 wt. % or less of MgO. MgO improves low temperature meltability, acid resistance and preservation stability under the humid environment. Therefore, although MgO is not an essential component of the low melting glass composition of the present disclosure, MgO is preferably contained with upper limit of the above ratio. In addition, when the content of MgO is surplus, acid resistance and preservation stability under the humid environment decrease. Therefore, when MgO is contained, it is preferable that the content of MgO is 3.0 wt. % or less. More preferably, the content of MgO is 2.3 wt. % or less.

It is preferable that the low melting glass composition of the present disclosure contains 3.0 wt. % or less of CaO. CaO improves low temperature meltability, acid resistance and preservation stability under the humid environment. Therefore, although CaO is not an essential component of the low melting glass composition of the present disclosure, CaO is preferably contained with upper limit of the above ratio. In addition, when the content of CaO is surplus, acid resistance and preservation stability under the humid environment decrease. Therefore, when CaO is contained, it is preferable that the content of CaO is 3.0 wt. % or less. More preferably, the content of CaO is 2.6 wt. % or less.

It is preferable that the low melting glass composition of the present disclosure contains 4.0 wt. % or less of $ZrO_2$. $ZrO_2$ improves acid resistance and preservation stability under the humid environment. Therefore, although $ZrO_2$ is not an essential component of the low melting glass composition of the present disclosure, $ZrO_2$ is preferably contained with upper limit of the above ratio. In addition, when the content of $ZrO_2$ is surplus, the glass easily becomes opaque and the melting point of the glass easily becomes high. Therefore, when $ZrO_2$ is contained, it is preferable that the content of $ZrO_2$ is 4.0 wt. % or less. More preferably, the content of $ZrO_2$ is 2.7 wt. % or less.

It is preferable that the low melting glass composition of the present disclosure contains 3.0 wt. % or less of $TiO_2$. $TiO_2$ improves acid resistance and preservation stability under the humid environment. Therefore, although $TiO_2$ is not an essential component of the low melting glass composition of the present disclosure, $TiO_2$ is preferably contained with upper limit of the above ratio. In addition, when the content of $TiO_2$ is surplus, the melting point of the glass easily becomes high. Therefore, when $TiO_2$ is contained, it is preferable that the content of $TiO_2$ is 3.0 wt. % or less. More preferably, the content of $TiO_2$ is 2.6 wt. % or less.

It is preferable that the low melting glass composition of the present disclosure contains 2.0 wt. % or less of F. F improves low temperature meltability. Therefore, although F is not an essential component of the low melting glass composition of the present disclosure, F is preferably contained with upper limit of the above ratio. In addition, when the content of F is surplus, it affect a decrease of acid resistance and preservation stability. Therefore, when F is contained, it is preferable that the content of F is 2.0 wt. % or less. More preferably, the content of F is 1.5 wt. % or less.

In the low melting glass composition having the above composition range, it is preferable that a thermal expansion coefficient based on ISO 6872:2015 is within a range of 7.0 to $11.0 \times 10^{-6}$ $K^{-1}$, preferably within a range of 7.5 to $9.5 \times 10^{-6}$ $K^{-1}$. One of main use methods of the low melting glass composition of the present disclosure is to laminate it in the upper part of a frame material (core material) such as lithium silicate glass ceramics and zirconia to prepare a dental crown prosthesis device. The thermal expansion coefficients of dental lithium silicate glass ceramics and zirconia are within a range of about 10.0 to $11.0 \times 10^{-6}$ $K^{-1}$. Therefore, a generation of crack on a preparation of a prosthesis device may be restrained by setting the expansion coefficient of the low melting glass composition of the present disclosure to a value which is slightly lower than the range of thermal expansion coefficient of dental lithium silicate glass ceramics and zirconia.

In the low melting glass composition having the above composition range, it is preferable that a dissolution amount to an acid based on ISO 6872:2015 is 35 μg/cm² or less, preferably 10 μg/cm² or less. The requirement value of this ISO standard is 100 μg/cm² of the dissolution amount. In the present disclosure, it is possible to prepare a low melting glass composition having a dissolution amount which is significantly below this requirement value.

The preparation of the low melting glass composition of the present disclosure can be performed by the common preparation method of the glass composition held by a person skilled in the art. In one of the common preparation method, various inorganic compounds are compounded so as to obtain a targeted composition to melt at 1300 to 1500° C. in a glass melting furnace. The melt is charged into water to be quenched (quenching) to prepare a glass frit.

In order to use the low melting glass composition of the present disclosure for a dental porcelain composition or a dental ceramics coloring material, it is required that the low melting glass composition is powdered. With respect to a powder preparation of the low melting glass composition, for example, there is a method of crushing the above glass flit by a crush machine such as ball mill, jet mill.

It is necessary to adjust the particle diameter of the powder of the low melting glass composition according to the characteristics of the targeted dental porcelain material or dental ceramics coloring material. In case of general dental porcelain material and dental ceramics coloring material, the mean particle size is 100 μm or less. When the object is to improve the operational characteristics of the powder and is to use in a thin layer, it is preferable that the mean particle size of the powder of the low melting glass composition which is a raw material is 50 μm or less.

When the low melting glass composition of the present disclosure is used for a dental porcelain material or a dental ceramics coloring material, it is possible to contain a pigment (colorant), a fluorescent pigment (fluorescent material) and an opaque material (opacifier) and the like without any limitation.

EXAMPLE

Hereinafter, the present invention will be described in detail with reference to Examples and Comparative Examples. However, the present invention is not limited to these Examples.

Evaluation methods of a thermal expansion coefficient, a softening point, acid resistance and preservation stability under the humid environment of the compositions in the Examples and Comparative Examples are shown below.
(Evaluation of Thermal Expansion Coefficient and Softening Point)

Each glass powder in Example and Comparative Example was kneaded with distilled water to prepare a kneaded material. The kneaded material was filled in a stick type mold made of the silicon (6×6×25 mm) and was subjected to condensation and water absorption repeatedly to prepare a molded body.

The molded body was taken out from the silicon mold and was calcined twice including one time vacuum calcination and one time atmospheric calcination by the dental technique porcelain furnace "Esthemat Slim" (manufactured by Shofu Inc.).

Sample was prepared by polishing both ends of the prepared twice calcined product to prepare parallel faces and adjusting the size to 5×5×20 mm. Thermal expansion coefficient and softening point of the sample was measured by the thermal expansion meter "TM8140C" (manufactured by Rigaku Corporation).
(Evaluation of Acid Resistance)

Each glass powder in Example and Comparative Example was kneaded with distilled water to prepare a kneaded material. The kneaded material was filled in a disk type mold made of the silicon (p 12 mm×2 mm) and was subjected to condensation and water absorption repeatedly to prepare a molded body. Ten samples were prepared by taking out the molded body from the silicon mold and vacuum calcination by the dental technique porcelain furnace "Esthemat Slim" (manufactured by Shofu Inc.). After surface polish of both surfaces of the samples, second calcination (atmospheric calcination) was performed. For the calcined samples, the test of solubility to acid was performed based on ISO 6872:2015
(Evaluation of Preservation Stability Under the Humid Environment)

Each glass powder in Example and Comparative Example was crushed to prepare glass powder. The glass powder was preserved for 30 days under the environment of 70° C. and 100% humidity. The preserved glass powder was kneaded with distilled water to prepare a kneaded material. The kneaded material was filled in a disk type mold made of the silicon (12 mm×2 mm) and was subjected to condensation and water absorption repeatedly to prepare a molded body. The molded body was taken out from the silicon mold and was vacuum calcined by the dental technique porcelain furnace "Esthemat Slim" (manufactured by Shofu Inc.) to prepare a sample. Transparency of the sample was evaluated by visual observation by comparing the standard sample which is before preservation under the humid environment. The rating criteria is as follows. A: Transparency was not impaired remarkably. B: Transparency was impaired remarkably.

Examples 1 to 20 and Comparative Examples 1 to 11

Various inorganic compounds were compounded and melted so as to achieve the glass compositions (wt. %) described in Table 1 to prepare glass flits according to Examples 1 to 20 and Comparative examples 1 to 11. The glass flit was crushed to prepare a glass powder having the mean particle size of 20 μm.

For the glass powder, tests of a thermal expansion coefficient, a softening point, acid resistance and preservation stability under the humid environment were performed. The results are shown in Table 2.

TABLE 1

| | Glass Composition (unit: wt. %) | | | | | | | | | | | |
|---|---|---|---|---|---|---|---|---|---|---|---|---|
| | $SiO_2$ | $B_2O_3$ | $Al_2O_3$ | ZnO | $Li_2O$ | $Na_2O$ | $K_2O$ | MgO | CaO | $ZrO_2$ | BaO | F |
| Example 1 | 70.3 | 6.4 | 3.0 | 8.2 | 2.8 | 4.7 | 4.6 | — | — | — | — | — |
| Example 2 | 67.1 | 7.8 | 5.6 | 4.2 | 3.4 | 3.6 | 8.3 | — | — | — | — | — |
| Example 3 | 67.7 | 10.1 | 2.4 | 4.3 | 3.4 | 3.7 | 8.4 | — | — | — | — | — |

TABLE 1-continued

| | Glass Composition (unit: wt. %) | | | | | | | | | | | |
|---|---|---|---|---|---|---|---|---|---|---|---|---|
| | $SiO_2$ | $B_2O_3$ | $Al_2O_3$ | ZnO | $Li_2O$ | $Na_2O$ | $K_2O$ | MgO | CaO | $ZrO_2$ | BaO | F |
| Example 4 | 65.6 | 7.6 | 5.5 | 4.1 | 3.8 | 4.1 | 9.3 | — | — | — | — | — |
| Example 5 | 65.9 | 8.0 | 5.8 | 4.3 | 1.9 | 3.7 | 8.5 | 1.9 | — | — | — | — |
| Example 6 | 65.5 | 7.9 | 5.7 | 4.3 | 1.9 | 3.7 | 8.4 | — | 2.6 | — | — | — |
| Example 7 | 65.8 | 7.6 | 5.5 | 4.2 | 3.3 | 3.6 | 8.1 | — | — | 1.9 | — | — |
| Example 8 | 63.9 | 7.4 | 5.4 | 4.0 | 3.7 | 4.0 | 9.1 | — | — | — | 2.5 | — |
| Example 9 | 66.4 | 7.7 | 5.6 | 4.2 | 3.4 | 3.6 | 8.2 | — | — | — | — | 0.9 |
| Example 10 | 65.5 | 7.9 | 5.7 | 4.3 | 1.9 | 3.7 | 8.4 | 1.2 | 1.4 | — | — | — |
| Example 11 | 64.0 | 7.5 | 3.6 | 7.5 | 3.5 | 13.9 | — | — | — | — | — | — |
| Example 12 | 64.0 | 7.5 | 3.6 | 7.5 | 3.5 | — | 13.9 | — | — | — | — | — |
| Example 13 | 75.0 | 6.1 | 2.0 | 6.4 | 2.5 | 4.0 | 4.0 | — | — | — | — | — |
| Example 14 | 55.0 | 12.0 | 8.0 | 5.0 | 5.5 | 14.5 | — | — | — | — | — | — |
| Example 15 | 70.4 | 7.4 | 5.7 | 2.0 | 2.9 | 3.6 | 8.0 | — | — | — | — | — |
| Example 16 | 70.3 | 6.1 | 3.0 | 8.5 | 2.8 | 4.7 | 4.6 | — | — | — | — | — |
| Example 17 | 60.0 | 9.0 | 5.5 | 6.5 | 5.0 | 14.0 | — | — | — | — | — | — |
| Example 18 | 70.0 | 6.5 | 7.0 | 4.0 | 3.0 | 4.8 | 4.7 | — | — | — | — | — |
| Example 19 | 68.7 | 7.8 | 4.0 | 4.2 | 3.4 | 3.6 | 8.3 | — | — | — | — | — |
| Example 20 | 67.2 | 7.6 | 5.5 | 2.5 | 3.8 | 4.1 | 9.3 | — | — | — | — | — |
| Comparative Example 1 | 64.3 | 4.1 | 8.3 | 9.4 | 3.2 | 5.4 | 5.3 | — | — | — | — | — |
| Comparative Example 2 | 62.7 | 7.7 | 3.6 | 9.8 | 0.0 | 16.2 | 0.0 | — | — | — | — | — |
| Comparative Example 3 | 71.2 | 7.4 | 5.7 | 1.2 | 2.9 | 3.6 | 8.0 | — | — | — | — | — |
| Comparative Example 4 | 60.8 | 12.2 | 3.5 | 9.5 | 3.2 | 5.4 | 5.4 | — | — | — | — | — |
| Comparative Example 5 | 76.4 | 5.1 | 2.4 | 6.5 | 2.2 | 3.7 | 3.7 | — | — | — | — | — |
| Comparative Example 6 | 68.0 | 8.5 | 6.5 | 8.0 | 3.5 | 5.5 | — | — | — | — | — | — |
| Comparative Example 7 | 61.0 | 7.5 | 3.0 | 6.5 | 6.5 | 15.5 | — | — | — | — | — | — |
| Comparative Example 8 | 68.0 | 8.5 | 6.5 | 8.0 | 3.5 | — | 5.5 | — | — | — | — | — |
| Comparative Example 9 | 61.0 | 7.5 | 3.0 | 6.5 | 6.5 | — | 15.5 | — | — | — | — | — |
| Comparative Example 10 | 69.7 | 9.0 | 6.5 | 5.5 | 1.8 | 2.0 | 5.5 | — | — | — | — | — |
| Comparative Example 11 | 63.4 | 7.6 | 3.0 | 4.2 | 4.5 | 8.0 | 9.3 | — | — | — | — | — |

TABLE 2

| | Thermal expansion coefficient (×10−6 K−1) | Softening point (° C.) | Acid resistant (dissolution amount) (μg/cm2) | Preservation stability under the humid environment |
|---|---|---|---|---|
| Example 1 | 7.5 | 575 | 30 | A |
| Example 2 | 8 | 563 | 1 | A |
| Example 3 | 8.5 | 566 | 13 | A |
| Example 4 | 7.8 | 547 | 5 | A |
| Example 5 | 7.9 | 581 | 1 | A |
| Example 6 | 7.8 | 591 | 3 | A |
| Example 7 | 8.6 | 572 | 8 | A |
| Example 8 | 7.8 | 557 | 2 | A |
| Example 9 | 8.5 | 545 | 4 | A |
| Example 10 | 7.9 | 586 | 3 | A |
| Example 11 | 9.4 | 539 | 13 | A |
| Example 12 | 7.9 | 569 | 20 | A |
| Example 13 | 7.1 | 592 | 24 | A |
| Example 14 | 8.2 | 552 | 33 | A |
| Example 15 | 7.8 | 574 | 3 | A |
| Example 16 | 7.5 | 577 | 28 | A |
| Example 17 | 10.2 | 532 | 26 | A |
| Example 18 | 7.2 | 588 | 23 | A |
| Example 19 | 8.1 | 568 | 2 | A |
| Example 20 | 8 | 539 | 12 | A |
| Comparative Example 1 | 9.1 | 562 | 17 | B |
| Comparative Example 2 | 7.3 | 612 | 126 | B |
| Comparative Example 3 | 8 | 580 | 12 | B |
| Comparative Example 4 | 8.5 | 553 | 602 | B |
| Comparative Example 5 | 7.5 | 578 | 4 | B |
| Comparative Example 6 | 7.8 | 559 | 90 | A |
| Comparative Example 7 | 11.1 | 493 | 67 | B |
| Comparative Example 8 | 9 | 568 | 208 | A |
| Comparative Example 9 | 9.7 | 537 | 62 | B |
| Comparative Example 10 | 5.3 | 599 | 182 | A |
| Comparative Example 11 | 10.3 | 524 | 1 | B |

In all Examples, a dissolution amount to an acid was 35 μg/cm² or less, which indicates that high acid resistance was exhibited and all examples were transparent, which indicates excellent preservation stability under the humid environment was exhibited.

On the other hand, in Comparative Examples 2, 4 and 6-10, a dissolution amount to an acid was more than 35 μg/cm², which indicates that sufficient acid resistance was not achieved. In Comparative Examples 1, 3, 5 and 11, transparency changed before and after the test of preservation stability, which indicates that sufficient preservation stability under the humid environment was not achieved.

In all Examples, a thermal expansion coefficient satisfied the range of 7.0 to $11.0\times10^{-6}$ $K^{-1}$ and a softening point was less than 600° C., which indicates that low temperature meltability was exhibited.

On the other hand, in a part of Comparative Examples, a thermal expansion coefficient deviated the range of 7.0 to $11.0\times10^{-6}$ $K^{-1}$ or a softening point deviated less than 600° C. In some Comparative Examples, a thermal expansion coefficient and a softening point satisfied the range. However, in the Comparative Examples, a dissolution amount to an acid was more than 35 μg/cm² or transparency changed before and after the test of preservation stability, which indicates that sufficient acid resistance was not achieved or sufficient preservation stability under the humid environment was not achieved.

As shown in the above results, the glass composition of the present disclosure exhibited excellent results which satisfies high acid resistance while maintaining low melting point and excellent preservation stability under the humid environment, which is not achieved by the conventional glass composition. It is considered the excellent results is caused by specific range of the oxide content in the glass composition.

Therefore, the glass composition of the present disclosure significantly improve acid resistance and preservation stability under the humid environment while maintaining ow temperature meltability of the conventional glass composition.

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty.

Accordingly, any such changes and modifications are intended to be included in the scope of the embodiments.

INDUSTRIAL APPLICABILITY

The present disclosure can be applied in industries because the present disclosure relates to a low melting glass composition and can be used for a dental porcelain and a dental ceramic coloring material.

What is claimed is:

1. A low melting glass composition with a softening point (Ts) less than 600° C., which comprises:
   $SiO_2$: 55.0 to 75.0 wt. %,
   $B_2O_3$: 6.1 to 12.0 wt. %,
   $Al_2O_3$: 2.0 to 8.0 wt. %,
   ZnO: 2.0 to 6.5 wt. %, and
   two or more alkali metal oxides: 10.5 to 20.0 wt. %,
     wherein a thermal expansion coefficient at a temperature within a range of 25° C. to 400° C. based on ISO 6872:2015 is within a range of 7.0 to $11.0\times10^{-6}$ $K^{-1}$.

2. The low melting glass composition according to claim 1, further comprising at least one selected from the group consisting of:
   MgO: 3.0 wt. % or less,
   CaO: 3.0 wt. % or less,
   $ZrO_2$: 4.0 wt. % or less,
   $TiO_2$: 3.0 wt. % or less, and
   F: 2.0 wt. % or less.

3. The low melting glass composition according to claim 1, wherein:
   a dissolution amount to an acid based on ISO 6872:2015 is 35 μg/cm² or less.

4. A dental porcelain compounded with the low melting glass composition according to claim 1.

5. A dental ceramics coloring material compounded with the low melting glass composition according to claim 1.

6. The low melting glass composition according to claim 2, wherein:
   a dissolution amount to an acid based on ISO 6872:2015 is 35 μg/cm² or less.

7. A dental porcelain compounded with the low melting glass composition according to claim 2.

8. A dental ceramics coloring material compounded with the low melting glass composition according to claim 2.

9. A dental porcelain compounded with the low melting glass composition according to claim 3.

10. A dental ceramics coloring material compounded with the low melting glass composition according to claim 3.

* * * * *